United States Patent
Woolston et al.

(10) Patent No.: US 7,637,899 B2
(45) Date of Patent: Dec. 29, 2009

(54) MEDICAMENT CARTRIDGE

(75) Inventors: Robert Woolston, Warwick (GB); Christopher Nigel Langley, Warwickshire (GB); Lee Simon Adams, Warwick (GB)

(73) Assignee: DCA Design International Limited, Warwick (GB)

( * ) Notice: Subject to any disclaimer, the term of this patent is extended or adjusted under 35 U.S.C. 154(b) by 791 days.

(21) Appl. No.: 10/307,300

(22) Filed: Dec. 2, 2002

(65) Prior Publication Data
US 2003/0153896 A1   Aug. 14, 2003

(30) Foreign Application Priority Data
Dec. 6, 2001   (GB)   ................... 0129171.5

(51) Int. Cl.
*A61B 19/00*   (2006.01)

(52) U.S. Cl. ........................ 604/415; 604/403

(58) Field of Classification Search ......... 604/195–236, 604/411–415
See application file for complete search history.

(56) References Cited

U.S. PATENT DOCUMENTS

| | | | |
|---|---|---|---|
| 3,150,661 A | 9/1964 | Maki | |
| 3,974,832 A | 8/1976 | Kruck | |
| 4,153,056 A * | 5/1979 | Silver et al. | ................. 604/211 |
| 5,135,514 A | 8/1992 | Kimber | |
| 5,226,901 A * | 7/1993 | Dhaliwal et al. | ............ 604/415 |
| 5,334,162 A * | 8/1994 | Harris | ........................ 604/232 |
| 5,389,086 A | 2/1995 | Attermeier et al. | |
| 5,454,786 A * | 10/1995 | Harris | ......................... 604/88 |
| 5,554,134 A * | 9/1996 | Bonnichsen | ................ 604/240 |
| 5,709,666 A * | 1/1998 | Reynolds | ..................... 604/191 |
| 5,989,227 A | 11/1999 | Vetter et al. | |
| 6,004,297 A | 12/1999 | Steenfeldt-Jensen et al. | |
| 6,126,646 A | 10/2000 | Hansen et al. | |

FOREIGN PATENT DOCUMENTS

| | | |
|---|---|---|
| CZ | 286 666 | 2/2000 |
| GB | 1 602 090 | 11/1981 |
| HU | 210 361 B | 2/1989 |
| HU | 222 513 B1 | 1/1999 |
| WO | WO 97 14461 | 4/1997 |
| WO | WO 99 16485 | 4/1999 |
| WO | WO 03/047667 A1 | 6/2003 |

\* cited by examiner

*Primary Examiner*—Leslie R Deak
(74) *Attorney, Agent, or Firm*—Oliff & Berridge, PLC

(57) ABSTRACT

Many of those having diabetes take a combination of slow and fast acting types of insulin. It is important that the different forms of medicament do not become confused. To this end, a medicament cartridge is provided comprising a sleeve having a bottleneck providing a flange at a first end, a fluid impermeable membrane secured across the first end by a metal cap beaded beneath the flange, and a displaceable piston located internally of the sleeve towards a second end of the sleeve, a collar located against an external periphery of the cartridge housing beneath the flange and an adaptor top press fit over the cap and the collar, the adaptor top being provided with means to act upon the collar thereby to retain the adaptor top on the sleeve.

30 Claims, 2 Drawing Sheets

MEDICAMENT CARTRIDGE

FIELD OF THE INVENTION

The present invention relates to improvements in and relating to medicament cartridges for use with medication delivery apparatus, and in particular but not exclusively to medicament cartridges for injector pens and infusers.

BACKGROUND TO THE INVENTION

It is known that a person providing themselves, or others, with a medicament regimen may require more than one medicament as part of that regimen. For example many of those having diabetes take a combination of slow and fast acting types of insulin. It is important that the different forms of medicament do not become confused and that the patient does not receive the incorrect medicament. It is thus advantageous that different forms of medicament are provided in medicament cartridges that can readily be distinguished.

However, in the manufacture of medicament cartridges, it is desirable, in order that advantage may be taken of economies of scale that as few different manufacturing steps as possible exist as between medicament cartridges contain different medicaments.

A number of solutions to this problem are already known. For example, in U.S. Pat. No. 6,126,646 an adaptor top for fitting to a medicament cartridge is disclosed. The adaptor top has a depending skirt the skirt being provided with an internally directed, circumferentially extending bead. The bead in use is seated beneath and against a metal cap of the medicament cartridge. In order to be placed over the cap the skirt is made very flexible or provided with a number of longitudinally extending slits. To prevent the skirt from being removed, a ring is placed over the skirt to prevent the beaded portion of the skirt from coming loose. However, should the ring in use become loose or inadvertently be dislodged, the adaptor top may easily or inadvertently become separated from the medicament cartridge.

The preset invention provides a further solution to the problem of balancing the requirements presented above.

SUMMARY OF THE INVENTION

According to the present invention a medicament cartridge comprises a sleeve having a bottleneck providing a flange at a first end, a fluid impermeable membrane secured across the first end by a metal cap beaded beneath the flange, and a displaceable piston located internally of tee sleeve towards a second end of the sleeve, a collar located against an external periphery of the cartridge housing beneath the flange and an adaptor top press fit over the cap and the collar, the adaptor top being provided with means to act upon the collar thereby to retain the adaptor top on the sleeve.

Since the collar is retrained within the adapt top there is no risk that it may work loose.

Preferably, the collar is adhered to the cartridge housing.

Preferably, the collar is defined by a first inner surface that cobs to a peripheral surface of the sleeve and a second outer surface. More preferably, the second outer surface provides a smooth rounded surface.

Preferably, the collar is formed as a hinged member.

Preferably the collar has a first end provided with a male coupling and a second end provided with a female coupling to received the male coupling.

BRIEF DESCRIPTION OF THE DRAWINGS

The invention will now be described by way of example only, with reference to the accompanying drawings in which:

FIG. 1 shows an exploded view of a medicament cartridge in accordance with the invention; and.

DETAILED DESCRIPTION OF THE INVENTION

Figure 1:
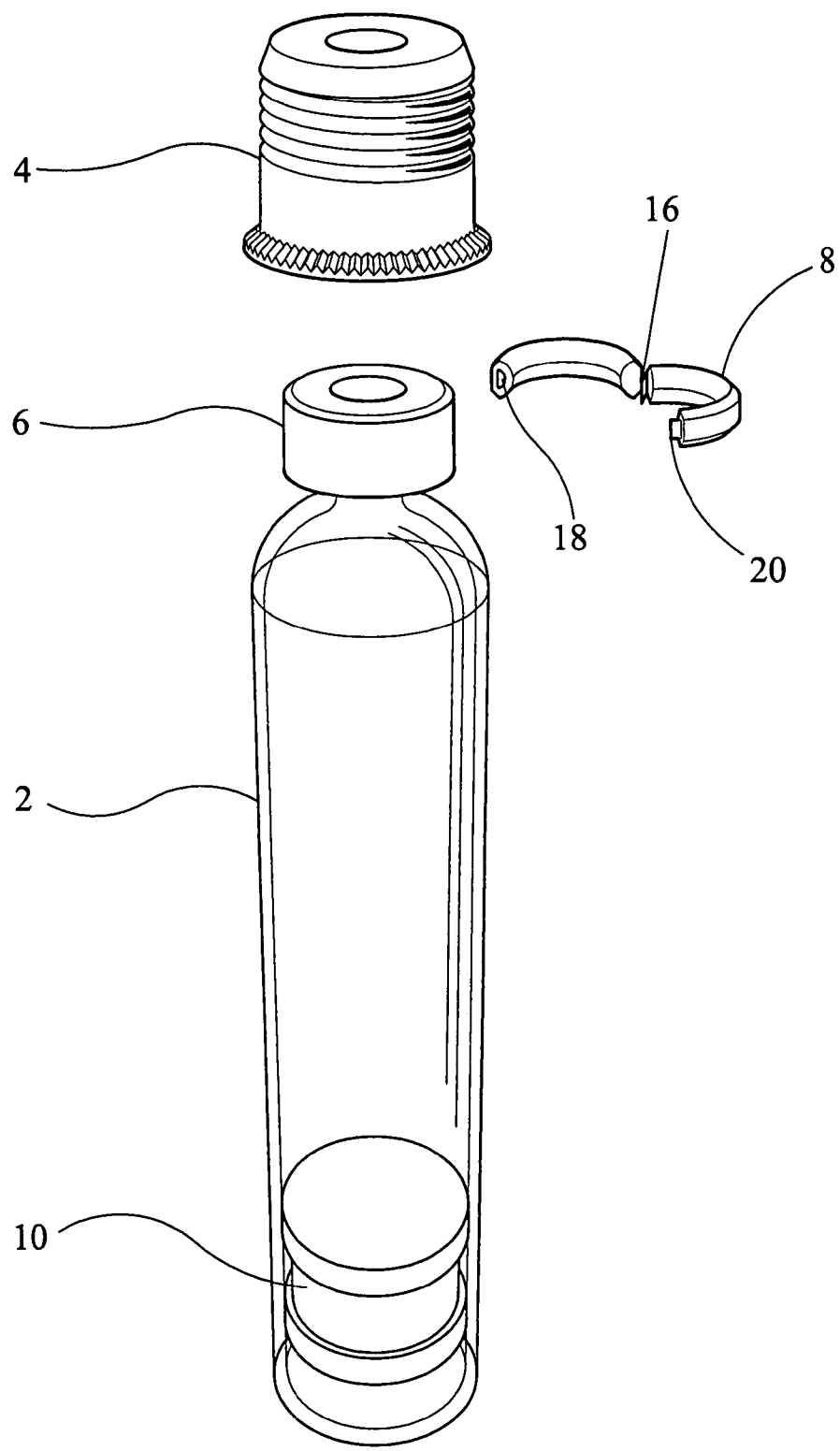
Figure 2:
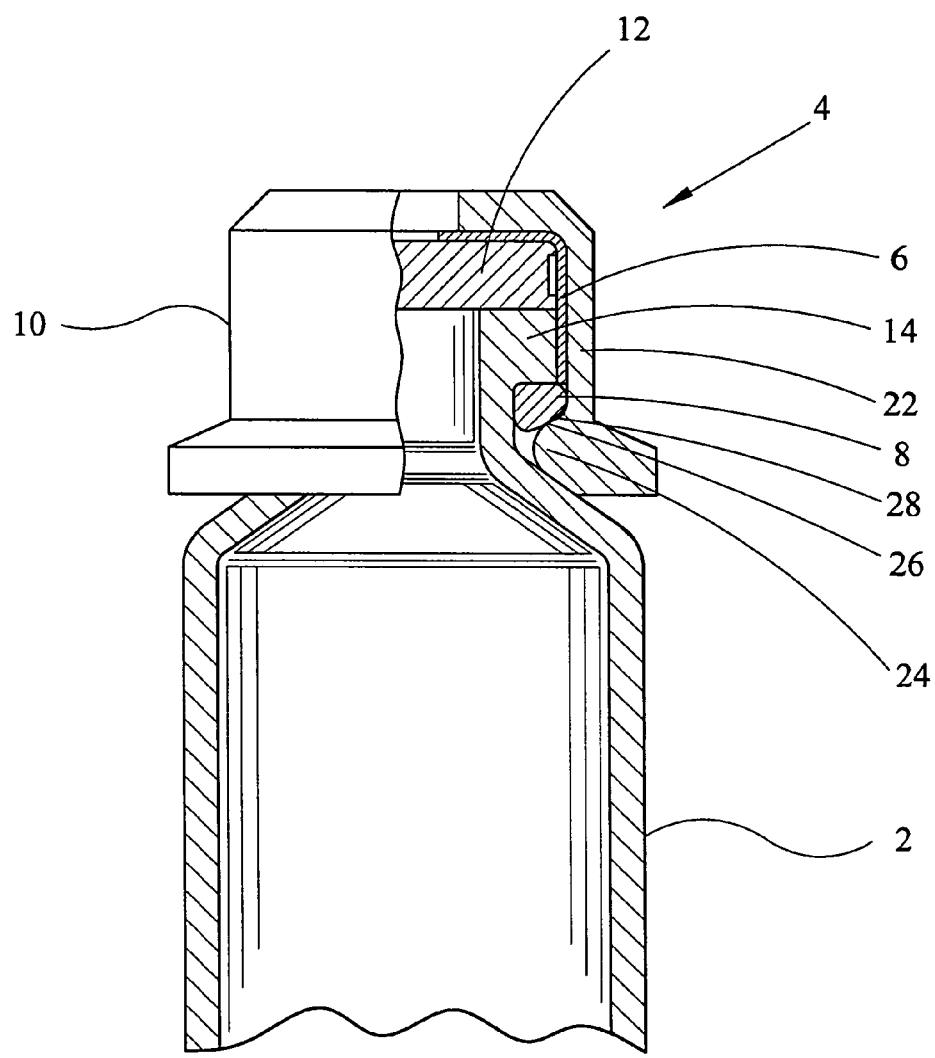
FIG. 2 shows a side section through an assembled medicament cartridge in accordance with the present invention.

Referring to FIG. 1 and FIG. 2, there may be seen a medicament cartridge 2 in accordance with the present invention.

The medicament cartridge comprise a cylinder, sleeve or cartridge housing 2 of a clear material such as a glass. A first end of the sleeve 2 is closed by a moveable on 10. A second end of the sleeve 2 is formed as a bottleneck having a flange 14, and is closed by a fluid impermeable membrane 12. A metal cap 6 extends over an upper surface of the membrane 12 and is beaded beneath the flame 14 to secure the membrane in position. An upper portion of the cap is provided with an aperture though which, in use, the membrane 12 may be pierced by a needle arrangement.

A collar 8 is also shown. In the illustrated embodiment the collar 8 is of hinged form. A hinge 16 separates a first end of the collar having a female coupling 18 from a second end of the collar 8 having a male coupling 20. In use, the male coupling 20 is received by the female coupling 18. The female coupling 18 and the male coupling 20 may be conveniently press fit or snap fit together.

An adaptor top 4 may then be pressed down over the metal cap 6 and the associated collar 8. The adaptor top 4 has peripheral skirt 22 provided with a radially directed internal flange or bead 24. The skirt 22 and the bead 24 are so disposed that when the adaptor top 4 is pressed down fully over the cap 6 and collar 8 an upper surface 26 of the bead 24 is in abutment with a lower surface 28 of the collar 8. This has the effect of retaining the adaptor top 4 in position.

The adaptor top 4 is formed from any suitable material. The adaptor top 4 should be made of a material sufficiently flexible that the peripheral skirt 22 can elastically deform about the metal cap 6, the collar 8 and the flange 14.

It will be understood that by manufacturing the adaptor top 4 of plastics material, the material may be colour coded to provide an indication of the nature of the medicament contained within the medicament cartridge.

The adaptor top 4 may conveniently be provided with a screw thread 30 or other means by which a needle unit may be secured to the medicament cartridge.

In order to dispense medicament from within the medicament cartridge, the piston 10 is urged towards the second end of the sleeve 2 to dispense medicament through a needle forming a part of the needle arrangement.

What is claimed is:

1. A medicament cartridge comprising a sleeve having a bottleneck providing a flange at a first end, a fluid impermeable membrane secured across the first end by a cap beaded beneath the flange, and a displaceable piston located internally of the sleeve towards a second end of the sleeve, a collar located against an external periphery of the cartridge housing beneath the flange, the collar being separate from the cap, and an adaptor top in a press fit over the cap and the collar, the adaptor top being provided with means to act upon the collar thereby to retain the adaptor top on the sleeve, the adaptor top being separate from the cap.

2. The medicament cartridge according to claim 1, wherein the collar is adhered to the sleeve.

3. The medicament cartridge according to claim 1, wherein the collar is defined by a first inner surface that conforms to a peripheral surface of the sleeve and a second outer surface.

4. The medicament cartridge according to claim 3, wherein the second outer surface provides a smooth rounded surface.

5. The medicament cartridge according to claim 1, wherein the collar is formed as a hinged member.

6. The medicament cartridge according to claim 1, wherein the collar has a first end provided with a male coupling and a second end provided with a female coupling to receive the male coupling.

7. The medicament cartridge according to claim 1, wherein the cap is made of metal.

8. The medicament cartridge according to claim 1, the sleeve being shaped so as to define an outer diameter that is smallest at a narrow section adjacent the flange, the collar extending only around the narrow section.

9. The medicament cartridge according to claim 8, the collar contacting an exterior surface of the narrow section of the sleeve.

10. The medicament cartridge according to claim 1, wherein the means to act upon the collar includes a bead portion that contacts the collar and the sleeve.

11. A cartridge usable to house medicament, the cartridge comprising:
- a sleeve having first and second ends, and a flange at the first end, the flange defining an exterior surface;
- a fluid impermeable membrane at the first end of the sleeve;
- a cap that communicates with the flange to retain the membrane at the first end of the sleeve;
- a displaceable piston located within the sleeve at the second end;
- a collar that contacts the exterior surface of the flange, the collar being separate from the cap; and
- an adaptor top that communicates with the collar to retain the adaptor top over the cap and the collar, the adaptor top being separate from the cap.

12. The cartridge according to claim 11, wherein the adaptor top is formed of a material to enable the adaptor top to be color coded to correspond to a particular medicament.

13. The cartridge according to claim 12, wherein the adaptor top is sufficiently flexible to elastically deform about the cap and the collar to retain the adaptor top over the cap and the collar.

14. The cartridge according to claim 13, wherein the adaptor top material is synthetic resin, and the cap is formed of metal.

15. The cartridge according to claim 11, wherein the cartridge is usable with a needle unit, and wherein the adaptor top defines an exterior surface that communicates with the needle unit to secure the adaptor top to the needle unit.

16. The cartridge according to claim 15, wherein the exterior surface of the adaptor top defines screw threads.

17. The cartridge according to claim 11, wherein the collar defines first and second ends, and a hinge between the first and second ends, the first and second ends being connectable to retain the collar at the exterior surface of the flange.

18. The cartridge according to claim 17, wherein the first end of the collar defines a female coupling, and the second end of the collar defines a male coupling that is receivable within the female coupling.

19. The cartridge according to claim 18, wherein the collar defines an inner surface that conforms to an exterior surface of the sleeve, and a smooth arcuate outer surface.

20. The medicament cartridge according to claim 11, wherein the adaptor top and the cap each define overlapping apertures over the membrane such that a portion of the membrane is exposed to an exterior of the cartridge.

21. The medicament cartridge according to claim 20, wherein the overlapping apertures are concentric.

22. The medicament cartridge according to claim 11, wherein the adaptor top includes a longitudinal skirt portion defining opposite first and second ends, a top portion adjacent the first end of the skirt portion and defining an aperture, and a bead portion adjacent the second end of the skirt portion.

23. The medicament cartridge according to claim 22, wherein the adaptor top is press fit over the cap and collar, such that the bead portion of the adaptor top contacts the collar, and the skirt portion of the adaptor top contacts the cap, to retain the adaptor top over the cap and the collar.

24. The medicament cartridge according to claim 11, wherein the membrane extends over the first end of the sleeve so as to not extend within the sleeve.

25. The cartridge according to claim 11, the sleeve being shaped so as to define an outer diameter that is smallest at a narrow section adjacent the flange, the collar extending only around the narrow section.

26. The cartridge according to claim 25, the collar contacting an exterior surface of the narrow section of the sleeve.

27. The cartridge according to claim 11, wherein the adaptor top includes a bead portion that contacts the collar and the sleeve.

28. A cartridge usable to house medicament, the cartridge comprising:
- a sleeve having first and second ends, and a flange at the first end, the flange defining an exterior surface;
- a fluid impermeable membrane at the first end of the sleeve;
- a cap that communicates with the flange to retain the membrane at the first end of the sleeve;
- a displaceable piston located within the sleeve at the second end;
- a collar that contacts the exterior surface of the flange; and
- an adaptor top that communicates with the collar to retain the adaptor top over the cap and the collar, the adaptor top being separate from the cap;
- wherein the adaptor top and the cap each define overlapping apertures over the membrane such that a portion of the membrane is exposed to an exterior of the cartridge.

29. The cartridge according to claim 28, wherein the overlapping apertures are concentric.

30. A cartridge usable to house medicament, the cartridge comprising:
- a sleeve having first and second ends, and a flange at the first end, the flange defining an exterior surface;
- a fluid impermeable membrane at the first end of the sleeve;
- a cap that communicates with the flange to retain the membrane at the first end of the sleeve;
- a displaceable piston located within the sleeve at the second end;
- a collar that contacts the exterior surface of the flange; and
- an adaptor top that communicates with the collar to retain the adaptor top over the cap and the collar, the adaptor top being separate from the cap;
- wherein the adaptor top includes a longitudinal skirt portion defining opposite first and second ends, a top portion adjacent the first end of the skirt portion and defining an aperture, and a bead portion adjacent the second end of the skirt portion; and
- wherein the adaptor top is press fit over the cap and collar, such that the bead portion of the adaptor top contacts the collar, and the skirt portion of the adaptor top contacts the cap, to retain the adaptor top over the cap and the collar.

* * * * *